United States Patent
Vogel (10) Patent No.: US 10,258,488 B2
(45) Date of Patent: Apr. 16, 2019

(54) STENT

(71) Applicant: Covidien LP, Mansfield, MA (US)

(72) Inventor: Jeffrey Vogel, Brooklyn Park, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/351,052

(22) Filed: Nov. 14, 2016

(65) Prior Publication Data

US 2018/0133038 A1    May 17, 2018

(51) Int. Cl.
*A61F 2/915* (2013.01)
*A61F 2/844* (2013.01)

(52) U.S. Cl.
CPC .............. *A61F 2/915* (2013.01); *A61F 2/844* (2013.01); *A61F 2002/91541* (2013.01); *A61F 2002/91575* (2013.01)

(58) Field of Classification Search
USPC .................................................. 623/1.1–3.1
See application file for complete search history.

(56) References Cited

U.S. PATENT DOCUMENTS

| | | | |
|---|---|---|---|
| 5,354,308 A | 10/1994 | Simon et al. | |
| 5,707,386 A | 1/1998 | Schnepp-Pesch et al. | |
| 5,718,713 A | 2/1998 | Frantzen | |
| 5,759,192 A | 6/1998 | Saunders | |
| 5,827,321 A * | 10/1998 | Roubin | A61F 2/91 623/1.16 |
| 5,843,164 A | 12/1998 | Frantzen et al. | |
| 5,843,175 A * | 12/1998 | Frantzen | A61F 2/91 623/1.15 |
| 5,860,999 A | 1/1999 | Schnepp-Pesch et al. | |
| 5,902,317 A | 5/1999 | Kleshinski et al. | |
| 6,042,606 A | 3/2000 | Frantzen | |

(Continued)

FOREIGN PATENT DOCUMENTS

| | | |
|---|---|---|
| CN | 1479596 | 3/2004 |
| CN | 101385669 | 3/2009 |

(Continued)

OTHER PUBLICATIONS

U.S. Appl. No. 15/351,082, naming Jeffrey Vogel et al., filed Nov. 14, 2016.

(Continued)

*Primary Examiner* — Yashita Sharma
(74) *Attorney, Agent, or Firm* — Shumaker & Sieffert, P.A.

(57) ABSTRACT

A stent includes a stent body defining a longitudinal axis and proximal and distal ends and being expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells and a plurality of peaks and valleys. The at least one intermediate segment defines only x number of cells. The first end segment defines at least x+1 number of cells. Each of the cells of the first end segment is substantially equal in size. Each of the at least one intermediate segment and the first end segment defines only y number of peaks and valleys.

20 Claims, 5 Drawing Sheets

(56) References Cited

U.S. PATENT DOCUMENTS

| | | | |
|---|---|---|---|
| 6,106,548 | A | 8/2000 | Roubin et al. |
| 6,190,406 | B1 | 2/2001 | Duerig et al. |
| 6,306,141 | B1 | 10/2001 | Jervis |
| 6,312,459 | B1 | 11/2001 | Huang et al. |
| 6,348,065 | B1 | 2/2002 | Brown et al. |
| 6,358,274 | B1 | 3/2002 | Thompson |
| 6,558,415 | B2 | 5/2003 | Thompson |
| 6,623,518 | B2 | 9/2003 | Thompson et al. |
| 6,699,278 | B2 | 3/2004 | Fischel et al. |
| 6,755,856 | B2 | 6/2004 | Fierens et al. |
| 6,814,746 | B2 | 11/2004 | Thompson et al. |
| 6,818,014 | B2 | 11/2004 | Brown et al. |
| 6,863,685 | B2 | 3/2005 | Davila et al. |
| 6,913,619 | B2 | 7/2005 | Brown et al. |
| 6,962,603 | B1 | 11/2005 | Brown et al. |
| 6,981,986 | B1 | 1/2006 | Brown et al. |
| 7,147,660 | B2 | 12/2006 | Chobotov et al. |
| 7,147,661 | B2 | 12/2006 | Chobotov et al. |
| 7,316,711 | B2 | 1/2008 | Allen et al. |
| 7,329,277 | B2 | 2/2008 | Addonizio et al. |
| 7,473,275 | B2 | 1/2009 | Marquez |
| 7,625,400 | B2 | 12/2009 | Bowe et al. |
| 7,655,033 | B2 | 2/2010 | Fearnot et al. |
| 7,753,948 | B2 | 7/2010 | Roeder et al. |
| 7,766,954 | B2 | 8/2010 | Chobotov et al. |
| 7,993,388 | B2 | 8/2011 | Lee et al. |
| 8,114,149 | B2 | 2/2012 | Fischell et al. |
| 8,167,927 | B2 | 5/2012 | Chobotov |
| 8,187,396 | B2 | 5/2012 | Parker |
| 8,211,162 | B2 | 7/2012 | Tischler et al. |
| 8,236,043 | B2 | 8/2012 | Caro et al. |
| 8,241,346 | B2 | 8/2012 | Chobotov |
| 8,328,864 | B2 | 12/2012 | Niermann |
| 8,328,865 | B2 | 12/2012 | Bales, Jr. et al. |
| 8,333,799 | B2 | 12/2012 | Bales, Jr. et al. |
| 8,382,816 | B2 | 2/2013 | Pollock et al. |
| 8,597,343 | B2 | 12/2013 | Bliss et al. |
| 8,628,565 | B2 | 1/2014 | Ta et al. |
| 8,658,081 | B2 | 2/2014 | Gale et al. |
| 9,180,031 | B2 | 11/2015 | Vogel et al. |
| 9,259,335 | B2 | 2/2016 | Vogel et al. |
| 9,610,180 | B2 | 4/2017 | Cam et al. |
| 2004/0138737 | A1 | 7/2004 | Davidson et al. |
| 2004/0167635 | A1 | 8/2004 | Yachia et al. |
| 2006/0015173 | A1 | 1/2006 | Clifford et al. |
| 2007/0050011 | A1* | 3/2007 | Klein ........................ A61F 2/91 623/1.16 |
| 2007/0061003 | A1 | 3/2007 | Shmulewitz et al. |
| 2007/0100434 | A1 | 5/2007 | Gregorich et al. |
| 2007/0239263 | A1 | 10/2007 | Fliedner |
| 2008/0221661 | A1 | 9/2008 | Bidne et al. |
| 2009/0105809 | A1 | 4/2009 | Lee et al. |
| 2009/0118810 | A1 | 5/2009 | Klein et al. |
| 2010/0137974 | A1 | 6/2010 | Chouinard et al. |
| 2012/0165920 | A1 | 6/2012 | Meyer et al. |
| 2012/0226346 | A1 | 9/2012 | Boismier et al. |
| 2014/0067045 | A1 | 3/2014 | Wack et al. |
| 2014/0128959 | A1 | 5/2014 | Gale et al. |
| 2014/0277379 | A1 | 9/2014 | Vogel et al. |
| 2014/0277380 | A1 | 9/2014 | Vogel et al. |
| 2015/0105852 | A1 | 4/2015 | Noffke et al. |
| 2015/0297378 | A1 | 10/2015 | Senness et al. |
| 2016/0022453 | A1 | 1/2016 | Vogel et al. |
| 2016/0120670 | A1 | 5/2016 | Vogel et al. |

FOREIGN PATENT DOCUMENTS

| | | |
|---|---|---|
| CN | 101516291 | 8/2009 |
| DE | 10144430 A1 | 3/2003 |
| DE | 102007060497 A1 | 6/2009 |
| EP | 1523959 A2 | 4/2005 |
| WO | 9725937 A1 | 7/1997 |
| WO | 2004/028571 A2 | 4/2004 |
| WO | 2007005800 A1 | 1/2007 |
| WO | 2007013102 A1 | 2/2007 |
| WO | 2008005535 A2 | 1/2008 |
| WO | 2009/137993 A1 | 11/2009 |
| WO | 2012096716 A2 | 7/2012 |
| WO | 2012143731 A1 | 10/2012 |

OTHER PUBLICATIONS

U.S. Appl. No. 15/351,007, naming Jeffrey Vogel et al., filed Nov. 14, 2016.

PCT/US2017/061210, The International Search Report and The Written Opinion of the International Searching Authority, dated Feb. 16, 2018, 14pgs.

PCT/US2017/061209, The International Search Report and The Written Opinion of the International Searching Authority, dated Feb. 16, 2018, 14 pgs.

* cited by examiner

STENT

TECHNICAL FIELD

This disclosure relates to a medical device and, in particular, to a stent.

BACKGROUND

Stents are widely used for numerous medical applications where the stent is placed in the lumen of a subject and expanded. Stents may be used in the coronary or the peripheral vasculature, as well as other body lumens. In some examples, stents are metal, tubular structures which are passed through a body lumen in a collapsed state. At the point of an obstruction or other deployment site in the body lumen, the stent is expanded to support the lumen. Stents may be self-expanding or balloon-expandable. Self-expanding stents may be inserted in a constrained state into a body lumen via a delivery device and released, such that the unconstrained stent is free to radially expand. A balloon-expandable stent may be positioned on a balloon of a balloon catheter and the stent is may be expanded at the deployment site through inflation of the balloon.

SUMMARY

In some aspects, this disclosure describes example stents, which may be vascular stents or arterial stents. A stent may include a stent body defining a longitudinal axis and proximal and distal ends. The stent body may be expandable from a compressed configuration to an expanded configuration. The stent body may include a plurality of stent segments, including a first end segment and a second end segment on opposite ends of the stent body and at least one intermediate segment disposed between the first end segment and the second end segment. Each stent segment may define a plurality of cells and a plurality of peaks and valleys. The at least one intermediate segment may define only x number of cells. The first end segment, which may be a proximal or distal end segment, may define at least x+1 number of cells. Each of the cells of the first end segment may be substantially equal in size. The at least one intermediate segment and the first end segment may each define only y number of peaks and valleys.

In some examples, the example stents may be formed by a method including selecting an appropriate diameter tubular member, forming the stent pattern described above in a tubular member to form the stent body, incrementally expanding and heat setting the tubular member, and heat setting the tube at its final diameter.

Clause 1: In some examples, a stent comprises a stent body defining a longitudinal axis and proximal and distal ends. The stent body is expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells. Each stent segment defines a plurality of peaks and valleys. The at least one intermediate segment defines only x number of cells. The first end segment defines at least x+1 number of cells. Each of the cells of the first end segment is substantially equal in size. The at least one intermediate segment defines only y number of peaks and valleys. The first end segment defines only y number of peaks and valleys.

Clause 2: In some examples of the stent of clause 1, a portion of the first end segment defining only one cell defines only three peaks, only two valleys, and only two half valleys, on each of two opposing sides of the portion of the first end segment.

Clause 3: In some examples of the stent of clause 1 or 2, a portion of the at least one intermediate segment defining only one cell defines only four peaks, only three valleys, and only two half valleys, on each of two opposing sides of the portion of the intermediate segment.

Clause 4: In some examples of the stent of any of clauses 1-3, the second end segment defines at least x+1 number of cells.

Clause 5: In some examples of the stent of any of clauses 1-4, each of the cells of the second end segment is substantially equal in size.

Clause 6: In some examples of the stent of any of clauses 1-5, a portion of the second end segment defining only one cell defines only three peaks, only two valleys, and only two half valleys, on each of two opposing sides of the portion of the second end segment.

Clause 7: In some examples of the stent of any of clauses 1-6, each of the cells of the at least one intermediate segment are substantially equal in size.

Clause 8: In some examples, a method comprises forming a stent pattern in a tubular member to form a stent body defining a longitudinal axis and proximal and distal ends. The stent body is expandable from a compressed configuration to an expanded configuration. The stent body includes a plurality of stent segments. The stent segments include a first end segment and a second end segment on opposite ends of the stent body and at least one intermediate segment disposed between the first end segment and the second end segment. Each stent segment defines a plurality of cells. Each stent segment defines a plurality of peaks and valleys. The at least one intermediate segment defines only x number of cells. The first end segment defines at least x+1 number of cells. Each of the cells of the first end segment is substantially equal in size. The at least one intermediate segment defines only y number of peaks and valleys. The first end segment defines only y number of peaks and valleys.

Clause 9: In some examples of the method of clause 8, the tubular member comprises shape-memory material.

Clause 10: In some examples of the method of clause 8 or 9, the method further comprises incrementally expanding and heat setting the tubular member.

Clause 11: In some examples of the method of any of clauses 8-10, a portion of the first end segment defining only one cell defines only three peaks, only two valleys, and only two half valleys, on each of two opposing sides of the portion of the first end segment.

Clause 12: In some examples of the method of any of clauses 8-11, a portion of the at least one intermediate segment defining only one cell defines only four peaks, only three valleys, and only two half valleys, on each of two opposing sides of the portion of the intermediate segment.

Clause 13: In some examples of the method of any of clauses 8-12, the second end segment defines at least x+1 number of cells.

Clause 14: In some examples of the method of any of clauses 8-13, each of the cells of the second end segment is substantially equal in size.

Clause 15: In some examples of the method of any of clauses 8-14, a portion of the second end segment defining only one cell defines only three peaks, only two valleys, and only two half valleys, on each of two opposing sides of the portion of the second end segment.

Clause 16: In some examples of the method of any of clauses 8-15, each of the cells of the at least one intermediate segment are substantially equal in size.

Clause 17: In some examples of the method of any of clauses 8-16, a portion of the first end segment defining only one cell defines only two peaks, only two half peaks, and only three valleys on each of two opposing sides of the portion of the first end segment.

Clause 18: In some examples, a method comprises advancing a distal end of a catheter to a treatment site within a patient, wherein a stent is disposed within the catheter; and releasing the stent from the catheter at the treatment site. The stent comprises a stent body defining a longitudinal axis and proximal and distal ends. The stent body is expandable from a compressed configuration to an expanded configuration. The stent body includes a plurality of stent segments. The stent segments include a first end segment and a second send segment on opposite ends of the stent body and at least one intermediate segment disposed between the first end segment and the second end segment. Each stent segment defines a plurality of cells. Each stent segment defines a plurality of peaks and valleys. The at least one intermediate segment defines only x number of cells. The first end segment defines at least x+1 number of cells. Each of the cells of the first end segment is substantially equal in size. The at least one intermediate segment defines only y number of peaks and valleys. The first end segment defines only y number of peaks and valleys.

Clause 19: In some examples of the method of a clause 18, the method further comprises inserting a guide member into a body lumen of the patient; and advancing the distal end of the catheter to the treatment site over the guide member.

Clause 20: In some examples of the method of a clause 18 or 19, a portion of the first end segment defining only one cell defines only three peaks, only two valleys, and only two half valleys, on each of two opposing sides of the portion of the first end segment.

Clause 21: In some examples of the method of any of clauses 18-20, a portion of the at least one intermediate segment defining only one cell defines only four peaks, only three valleys, and only two half valleys, on each of two opposing sides of the portion of the intermediate segment.

Clause 22: In some examples of the method of any of clauses 18-21, the second end segment defines at least x+1 number of cells.

Clause 23: In some examples of the method of any of clauses 18-23, each of the cells of the second end segment is substantially equal in size.

Clause 24: In some examples of the method of any of clauses 18-23, a portion of the second end segment defining only one cell defines only three peaks, only two valleys, and only two half valleys, on each of two opposing sides of the portion of the second end segment.

Clause 25: In some examples of the method of any of clauses 18-24, each of the cells of the at least one intermediate segment are substantially equal in size.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

A medical stent, e.g., a vascular stent or an arterial stent, may be configured such that certain mechanical characteristics of the stent, such as lateral and radial strength, fracture resistance, and uniform strain distribution, are balanced with stent flexibility in both the longitudinal and radial directions. A stent may be flexible in order to accommodate movement at the implantation site within a patient. For example, a stent may be positioned within a subject's vasculature at or near a subject's joint (e.g., hip, pelvis, knee, elbow, etc.). In these regions, the stent may be subjected to torsion, bending and other mechanical stress. Moreover, stents for use in the venous system such as inferior vena cava (IVC), common iliac, external iliac, and common femoral veins regions require relatively high strength and maximum flexibility, e.g., compared with stents configured for use in other implant sites, such as arterial implant sites.

In some cases, an end of a stent (e.g., a distal or proximal end, or both the distal and proximal ends, which may be terminal ends of the stent) may have different performance requirements than the middle of the stent. Flexibility, radial force (e.g., force in radially outward directions from a center axis of the stent) and lateral force (e.g., force in a single lateral direction), and durability requirements may each be somewhat different for the end of the stent than for the middle. In addition, the end may play a particularly important role with respect to ease of deployment of the stent in a body lumen of a patient and/or deployment accuracy.

The example stents described herein may accomplish particular technical advantages. For example, the modification of at least one end segment of the stent, such that it has a different configuration than the intermediate segments of the stent (located between the end segments), including a greater number of cells (e.g., due to a greater number of struts, a greater number of connectors between struts, or both) than the intermediate segments, may improve ease of deployment and/or deployment accuracy when compared to stents without modification to any of the end segments (with the same configuration in the intermediate segments and the end segments). The configuration of the end segments of the stent may allow the stent to be deployed more smoothly (e.g. may experience less "jump") from a delivery device (e.g., a delivery catheter), which may allow the stent to be more easily, predictably, and accurately deployed in an intended site within a body lumen of a patient without the stent jumping out of the delivery device (e.g., as an outer sheath is retracted) and away from the intended target site.

The example stents described herein may also accomplish particular technical advantages compared to end segments including the same number of struts but twice the number of evenly sized cells as the intermediate segments. For example, the example stents may have increased flexibility over such designs without substantial reduction in radial or lateral force. With increased flexibility in the end segments, overlapped stents may have smoother flexibility transitions in a region of overlap (e.g., defined by end segments of the overlapped stents) and, therefore, improved durability in an overlapped configuration.

In some examples, a stent includes a stent body defining a longitudinal axis and proximal and distal ends. The stent body may be expandable from a compressed configuration to an expanded configuration. The stent body may include a plurality of stent segments, including a first end segment and a second end segment on opposite ends of the stent body and at least one intermediate segment disposed between the first end segment and the second end segment. Each stent segment may define a plurality of cells and a plurality of peaks and valleys. The at least one intermediate segment may define only x number of cells. The first end segment may define at least x+1 number of cells. Each of the cells of the first end segment may be substantially equal in size. The at least one intermediate segment may define only y number of peaks and valleys. The first end segment may define only y number of peaks and valleys.

In some examples, the example stents may be formed by a method including selecting an appropriate diameter tubular member, forming the stent pattern described above in a tubular member to form the stent body, incrementally expanding and heat setting the tubular member, and heat setting the tube at its final diameter.

Although the figures below illustrate stents with a particular number of segments, the number of segments may vary depending on the type of interventional procedure and the desired length of the stent.

The stents of the present disclosure may have particular application in an iliofemoral vein of a patient. However, the stents may be used in any suitable location of the vasculature or other body lumen.

Figure 1A:
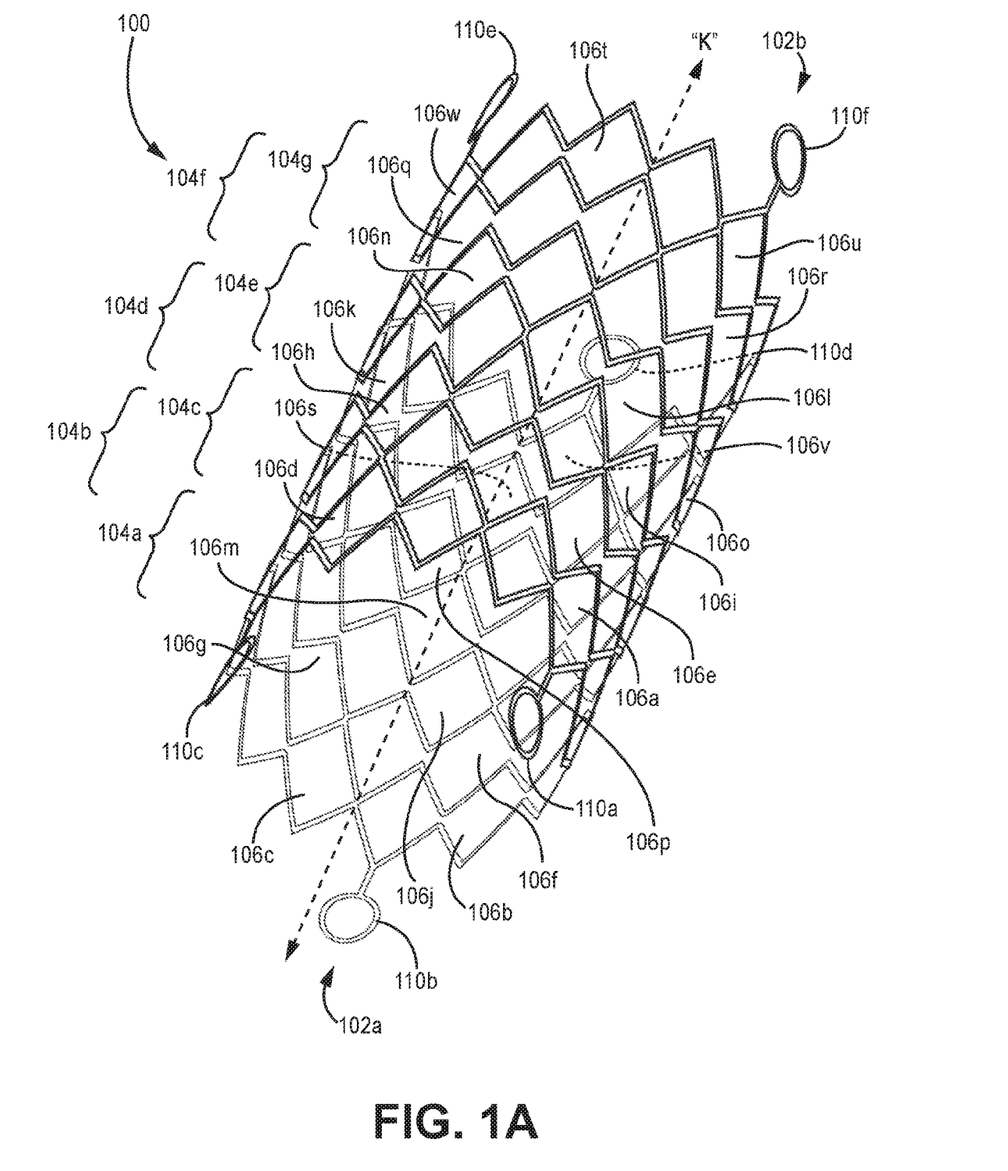
FIG. 1A is a perspective view of an example stent in an expanded condition.
Figure 1B:
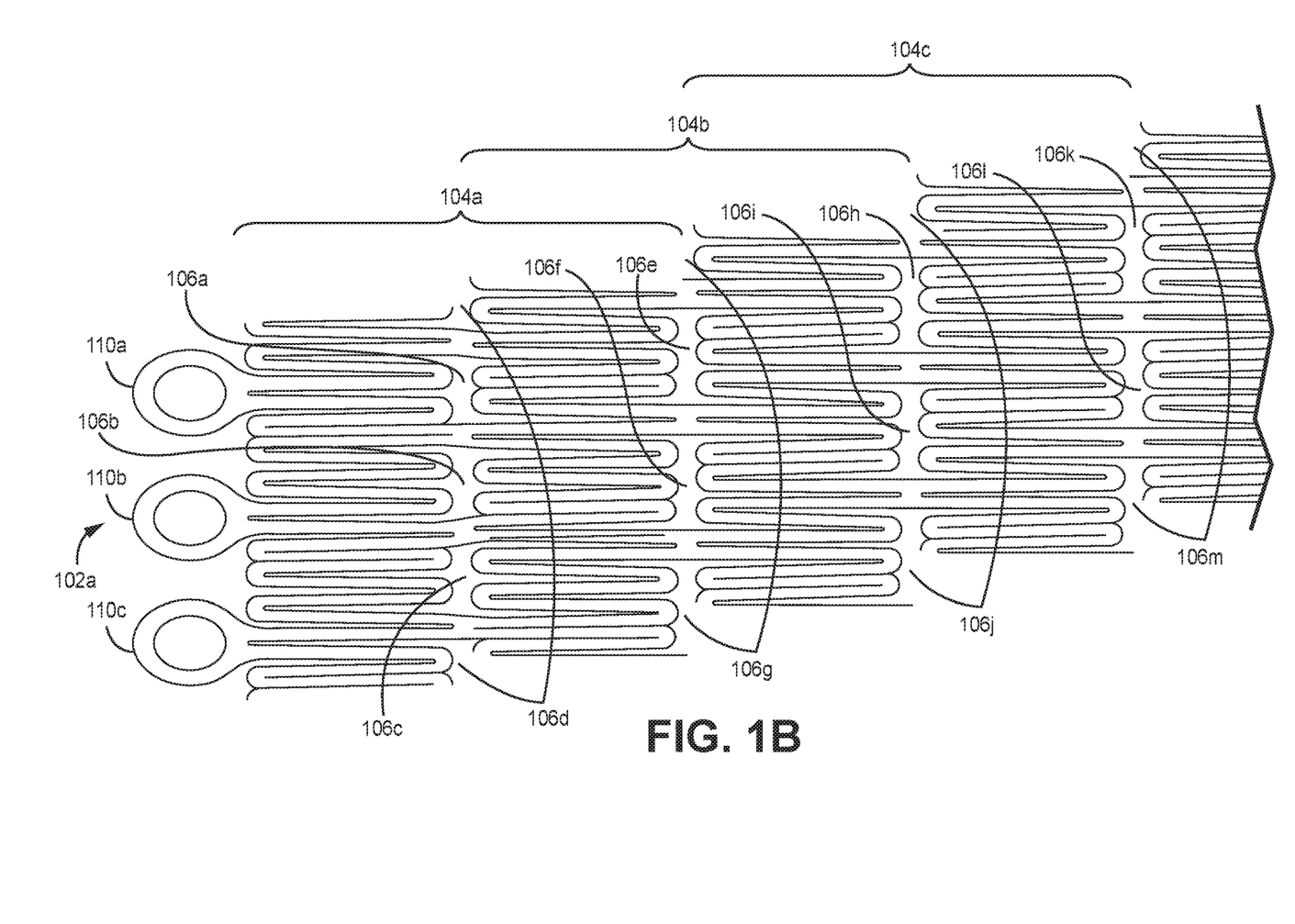
FIG. 1B is a plan view of a portion of the stent of FIG. 1A unrolled, laid flat, and in an unexpanded condition.
Figure 1C:
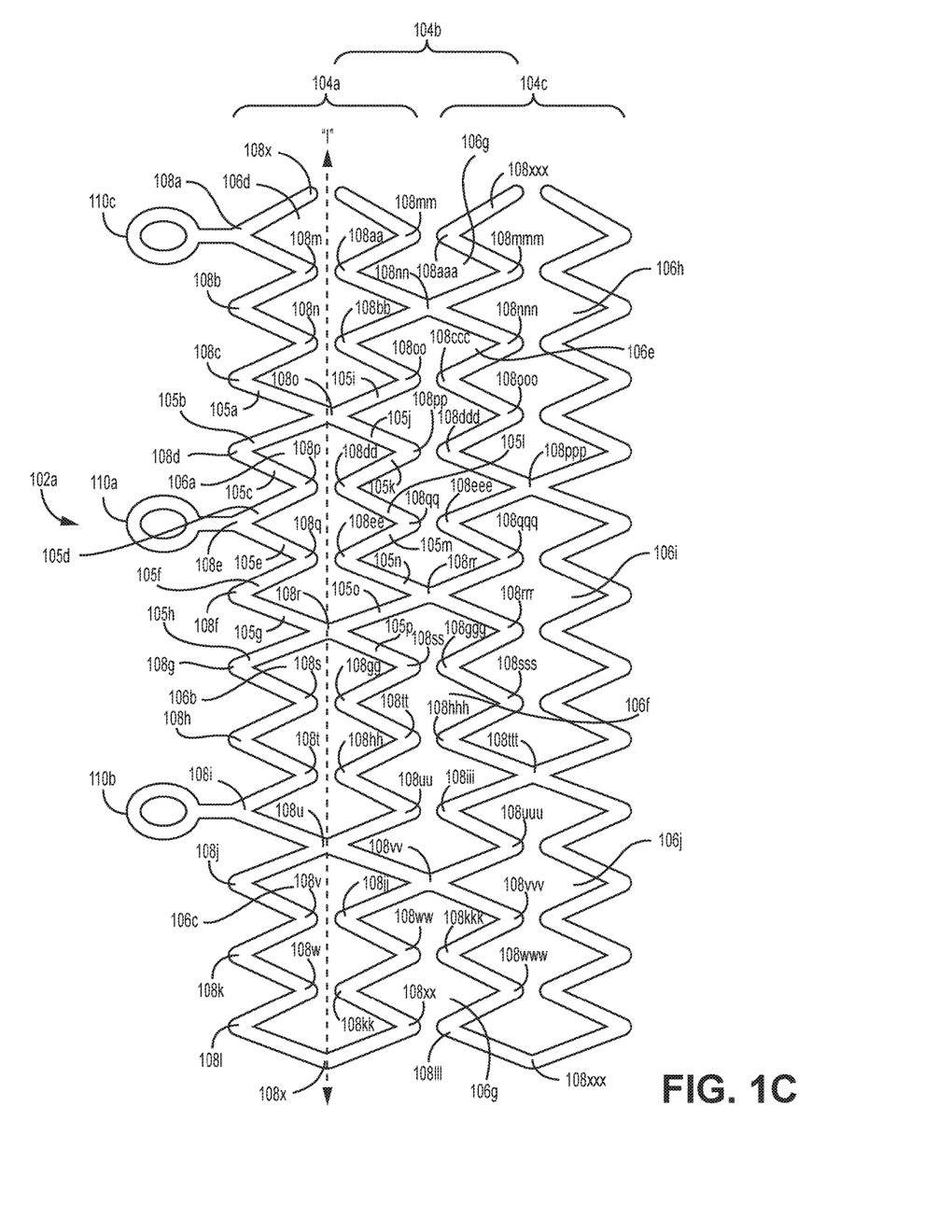
FIG. 1C is a plan view of a portion of the stent of FIG. 1A unrolled, laid flat, and in an expanded condition.

FIG. 1A is a perspective view of an example stent in an expanded condition. FIG. 1B is a plan view of a portion of the stent of FIG. 1A unrolled, laid flat, and in an unexpanded condition. FIG. 1C is a plan view of a portion of the stent of FIG. 1A unrolled, laid flat, and in an expanded condition. In the example shown in FIGS. 1A-1C, the stent comprises a stent body 100 defining a longitudinal axis "k," a proximal end 102a, and a distal end 102b. The stent body 100 may be expandable from a compressed configuration, as shown in FIG. 1B, to an expanded configuration, as shown in FIGS. 1A and 1C.

In a compressed configuration, the stent body 100 may define a smaller profile (e.g., a smaller outer perimeter in a cross-section taken perpendicular to longitudinal axis "k", which may be an outer diameter in examples in which the stent body 100 is round in cross-section). The stent body 100 may be compressed for, example, before deployment at a treatment site, including when the stent body 100 is being delivered to the treatment site. The compressed configuration of the stent body 100 may allow for a lower profile delivery system, due at least in part to the smaller profile stent body 100, which may increase the ease with which the stent body 100 may be delivered to a treatment site within a body lumen.

In some examples, the stent body 100 may be biased to an expanded configuration but may be compressed and constrained, for example, by a sheath of a delivery catheter until deployment of the stent body 100 from the delivery catheter. For example, the stent body 100 may formed from a shape memory material, such as, but not limited to, a nickel titanium alloy. The stent body 100 may be deployed at a treatment site by, for example, retraction of the sheath of the delivery catheter which may allow for the stent body 100 to expand into the body lumen. In some examples, the stent body 100 may not be biased to an expanded configuration and may be expanded at the delivery site by, for example, a balloon catheter or another mechanism suitable for expanding the stent body 100 from the compressed configuration to the expanded configuration. For example, the stent body 100 may be formed from stainless steel or another suitable non-self-expanding material.

The stent body 100 may include a plurality of stent segments 104a-104g (collectively referred to herein as "stent segments 104"). Each of the stent segments 104 may be defined by a pair of adjacent circumferential rows of struts, where each row of struts extends in a circumferential direction. Adjacent stent segments, such as stent segments 104a and 104b, may share a common row of struts. Example struts are shown as struts 105a-105o in FIG. 1C, and the struts of the stent body 100 may be collectively referred to as struts 105. Each of the struts 105 may be a substantially straight portion (e.g., a straight or nearly straight member) of the stent body 100 that may join with one or more other struts at a vertex 108. For example, the strut 105b is a substantially strait portion of the stent body 100 that joins with the struts 105a, 105i, and 105j at the vertex 108o and joins with the strut 105c at the vertex 108d. As another example, the strut 105c is a straight portion of the stent body 100 that joins with the strut 105b at the vertex 108d and joins with the strut 105d at the vertex 108p. In some examples, the struts 105 may each remain substantially straight before and after expansion of the stent body 100. However, the struts 105 may move relative to each other, e.g., pivoting at the vertices relative to adjacent struts, when the stent body 100 expands from the compressed configuration to the expanded configuration.

Although the stent body 100 is illustrated in FIG. 1A as including the seven overlapping stent segments 104a-104g and four independent, non-overlapping stent segments 104a, 104c, 104e, and 104g), in the other examples, the stent body 100 may include any suitable number of stent segments 104 according to particular needs. For example, in applications requiring a shorter stent, the stent body 100 may include a smaller number of stent segments 104, such as three, four, or five stent segments. As another example, in applications requiring a longer stent, the stent body 100 may include a larger number of stent segments 104. In some examples, each of the stent segments 104 may be shorter and/or longer such that a greater or fewer number of total stent segments 104 may result in a stent body 100 with the same length.

The stent segments 104 of the stent body 100 include an end segment 104a located at the proximal end 102a of the stent body 100 and an end segment 104g at the distal end 102b of the stent body 100. Each of the end segments 104a and 104g may be located at an end of the stent body 100 so that it is only adjacent one other stent segment. The stent segments 104 further include at least one intermediate segment 104b-104f disposed between the end segment 104a and the end segment 104g.

The struts of each of the stent segments 104 may define a plurality of cells 106, which may each be a closed cell defined by surrounding struts and each defining a single opening. For example, the end segment 104a may define the cells 106a-106d, the intermediate segment 104b may define the cells 106e-106g, and the end segment 104g may define the cells 106t-106w. In some examples, each of the cells

106*a*-106*d* of the end segment 104*a* may be substantially equal in size. In addition, in some examples, each of the cells 106*e*-106*g* of the intermediate segment 104*b* may be substantially equal in size. In some examples, each of the cells 106*t*-106*w* of the end segment 104*g* may be substantially equal in size. For example, in some examples, each of the cells 106*a*-106*d*, 106*t*-106*w* of the end segments 104*a*, 104*g*, alone or in combination with each of the cells of the intermediate segments, may be substantially equal in size.

In some examples, the terminal ends 110*a*-110*f* are configured to help retain the stent body 100 on a delivery device (e.g., configured to mate with structures on a delivery device). In addition, in some examples, one or more terminal ends 110*a*-110*f* may be radiopaque or may include radiopaque elements, which may be configured to aid a clinician in visualizing the position of the stent body 100 within a body lumen.

The struts 105 of end segment 104*a* are configured to define a plurality of peaks and valleys. A peak may be a vertex 108 that, together with the adjacent struts 105 forming the vertex, points in a distal or proximal direction away from a longitudinal center of the stent segment comprising the cell. For example, the struts 105*b* and 105*c* join at the vertex 108*d* to form a peak pointing in a proximal direction away from a longitudinal center of the stent segment 104*a*. The longitudinal center of the stent segment 104*a* is shown by the line labeled "1" in FIG. 1C. As another example, the struts 105*j* and 105*k* join at the vertex 108*pp* to form a peak pointing in a distal direction away from the longitudinal center of the stent segment 104*a*. A valley may be a vertex that, together with the adjacent struts forming the vertex, points in a distal or proximal direction toward the longitudinal center of the stent segment comprising the cell. For example, the struts 105*c* and 105*d* join at the vertex 108*p* to form a valley pointing in a distal direction toward the longitudinal center of the stent segment 104*a*. As another example, the struts 105*k* and 105*l* join at the vertex 108*dd* to form a valley pointing in a proximal direction toward the longitudinal center of the stent segment 104*a*. In some cases, the vertex of a valley may be located at the longitudinal center of the stent segment comprising the cell. For example, the struts 105*a*, 105*b*, 105*i*, and 105*j* join at the vertex 108*o* at the longitudinal center of the stent segment 104*a*, the struts 105*a* and 105*b* form at valley pointing in a distal direction, and the struts 105*i* and 105*j* form a valley pointing in a proximal direction.

The vertices 108*a*-108*l* and 108*mm*-108*xx* may correspond to a plurality of peaks defined by the end segment 104*a* and the vertices 108*m*-108*x*, 108*aa*, 108*bb*, 108*o*, 108*dd*, 108*ee*, 108*r*, 108*gg*, 108*hh*, 108*u*, 108*j*, 108*kk*, and 108*x* may correspond to a plurality of valleys defined by the end segment 104*a*. In some examples, the intermediate segment 104*b* may define a plurality of peaks and valleys. For example, the vertices 108*aa*, 108*bb*, 108*o*, 108*dd*, 108*ee*, 108*r*, 108*gg*, 108*hh*, 108*u*, 108*jj*, 108*kk*, 108*x* and 108*mmm*-108*xxx* may correspond to a plurality of peaks defined by the intermediate segment 104*b* and the vertices 108*mm*-108*xx*, 108*aaa*, 108*nn*, 108*ccc*-108*eee*, 108*rr*, 108*ggg*-108*iii*, 108*vv*, 108*kkk*, and 108*lll* may correspond to a plurality of valleys defined by the intermediate segment 104*b*.

In some examples, at least one of the end segment 104*a* or the end segment 104*g* (e.g., one of the end segments 104*a* or 104*g*, or both of the end segments 104*a* and 104*g*) may define more cells than at least one of the intermediate segments 104*b*-104*f*. For example, the intermediate segment 104*b* and/or any of the intermediate segments 104*c*-104*f*, may define x number of cells and the end segment 104*a*, the end segment 104*g*, or both of the end segments 104*a*, 104*g* may define at least x+1 number of cells. As an example, in the illustrated example, the intermediate segment 104*b* defines the three cells 106*e*, 106*f*, and 106*g*, the end segment 104*a* defines four cells 106*a*, 106*b*, 106*c*, and 106*d*, and the end segment 105*g* defines the four cells 106*t*, 106*u*, 106*v*, and 106*w*.

In some examples, each of the stent segments 104*a*-104*g* may define the same number of peaks and valleys. For example, in the illustrated example, each of the stent segments 104*a*-104*g* defines 24 peaks and 24 valleys. For example, the end segment 104*a* defines 24 peaks, each corresponding to one of the vertices 108*a*-108*l* and 108*mm*-108*xx*, and defines 24 valleys, each corresponding to one of the vertices 108*m*-108*x*, 108*aa*, 108*bb*, 108*o*, 108*dd*, 108*ee*, 108*r*, 108*gg*, 108*hh*, 108*u*, 108*j*, 108*kk*, and 108*x*; and the intermediate segment 104*b* defines 24 peaks, each corresponding to one of the vertices 108*aa*, 108*bb*, 108*o*, 108*dd*, 108*ee*, 108*r*, 108*gg*, 108*hh*, 108*u*, 108*j*, 108*kk*, 108*x* and 108*mmm*-108*xxx*, and defines 24 valleys, each corresponding to one of the vertices 108*mm*-108*xx*, 108*aaa*, 108*nn*, 108*ccc*, 108*ddd*, 108*eee*, 108*rr*, 108*ggg*, 108*hhh*, 108*iii*, 108*w*, 108*kkk*, and 108*lll*.

In some examples, larger cells may be defined by more surrounding struts than smaller cells and may define more peaks and valleys than smaller cells. For example, each of the cells 106*a*, 106*b*, 106*c*, and 106*d* may be defined by twelve surrounding struts and each of the cells 106*e*, 106*f*, and 106*g* may be defined by sixteen surrounding struts. For example, the cell 106*b* may be defined by the twelve surrounding struts 105*b*, 105*c*, 105*d*, 105*e*, 105*f*, 105*g*, 105*j*, 105*k*, 105*l*, 105*m*, and 105*n*. Also for example, each of two opposing sides of each of the cells 106*a*, 106*b*, 106*c*, and 106*d* may define three peaks, two valleys, and two half-valleys and each of two opposing sides of each of the cells 106*e*, 106*f*, and 106*g* may define four peaks, three valleys, and two half-valleys. For example, each of two opposing sides of the cell 106*a* may define three peaks, formed at the vertex 108*d* between the struts 105*b* and 105*c*, the vertex 108*e* between the struts 105*d* and 105*e*, and at the vertex 108*f* between the struts 105*f* and 105*g* on one side and formed by the vertex 108*pp* between the struts 105*j* and 105*k*, by the vertex 108*qq* between the struts 105*l* and 105*m*, and by the vertex 108*rr* between the struts 105*n* and 105*o* on the other side, two valleys, formed at the vertex 108*p* between the struts 105*c* and 105*d* and at the vertex 108*q* between the struts 105*e* and 105*f* on one side and formed by the vertex 108*dd* between the struts 105*k* and 105*l* and at the vertex 108*ee* between the struts 105*m* and 105*n* on the other side, and two half valleys, formed by the struts 105*b* and 105*f* on one side and by the struts 105*j* and 105*n* on the other side. A half-valley may be one half of a valley, as defined by one strut defining the cell, and may combine with another half-valley, as defined by an adjacent strut defining an adjacent cell, to form the valley. For example, the strut 105*b* may define one half of a valley and the strut 105*a* may define one half valley, such that the two half-valleys may join at the vertex 108*o* to form a whole valley.

In other words, a portion of the end segment 104*a* defining only one cell defines only three peaks, only two valleys, and only two half-valleys on each of two opposing sides of the portion of end segment 104*a* (i.e., each circumferential row of struts defining either side of the respective stent segment). For example, the portion of the end segment 104*a* defining the cell 106*a* may define three peaks, corresponding to the vertices 108*d*, 108*e*, and 108*f*, two valleys, corresponding to the vertices 108p and 108q, and two half-valleys, corresponding to the vertices 108o and 108r, on one side and may define three peaks, corresponding to the vertices 108pp, 108qq, and 108rr, two valleys, corresponding to the vertices 108dd and 108ee, and two half-valleys, corresponding to the vertices 108cc and 108ff, on the other side.

In some examples, a portion of the intermediate segment 104v defining only one cell defines only four peaks, only three valleys, and only two half valleys, on each of two opposing sides of the portion of the intermediate segment. For example, the portion of the intermediate segment 104b defining the cell 106e may define four peaks, corresponding to the vertices 108bb, 108cc, 108dd, and 108ee, three valleys, corresponding to the vertices 108oo, 108pp and 108qq, and two half-valleys, corresponding to the vertices 108nn and 108rr, on one side and may define four peaks, corresponding to the vertices 108nnn, 108ooo, 108ppp, and 10qqq, three valleys, corresponding to the vertices 108ccc, 108ddd, and 108eee, and two half-valleys, corresponding to the vertices 108bbb and 108fff, on the other side.

In some examples, a portion of the end segment 106g defining only one cell defines only three peaks, only two valleys, and only two half valleys, on each of two opposing sides of the portion of the end segment 104g.

The end segments of stent bodies described herein, including the stent body 100 shown in FIGS. 1A-1C, may have different performance requirements than the middle of the stent. For example, the configuration of the end segments may help improve the ease of deployment of the stent in a body lumen of a patient and/or deployment accuracy. For example, although a greater number of cells and smaller cells in the end segments may decrease flexibility of the end segments, they may help increase the ease of deployment and/or deployment accuracy of the stent in a body lumen.

The pattern of the cells 106 of the end segments 104a and 104g of the stent body 100 as described herein, which have a different configuration than the intermediate segments of the stent body 100, including a greater number of cells than the intermediate segments and smaller cells than the cells of the intermediate segments (i.e. cells surrounded by fewer struts and including fewer peaks and valleys than the cells of the intermediate segments), may improve ease of deployment and/or deployment accuracy compared to stents with the same configuration in the end and intermediate segments. For example, the stent may be deployed more smoothly (e.g., may experience less "jump") from a delivery device, such that the stent may be more easily, predictably, and accurately deployed in an intended site in a body lumen of a patient without the stent jumping out of the delivery device and away from the intended target site.

The pattern of the cells 106 of the end segments 104a and 104g of the stent body 100 as described herein may also accomplish particular technical advantages compared to stents with end segments including the same number of struts but twice the number of evenly sized cells as intermediate segments. For example, the end segments 104a and 104g may have increased flexibility over such designs without a substantial reduction in radial force or lateral force. With increased flexibility in the end segments 104a and 104g, overlapped stents may have smoother flexibility transitions in a region of overlap and, therefore, improved durability in an overlapped configuration.

Figure 2:
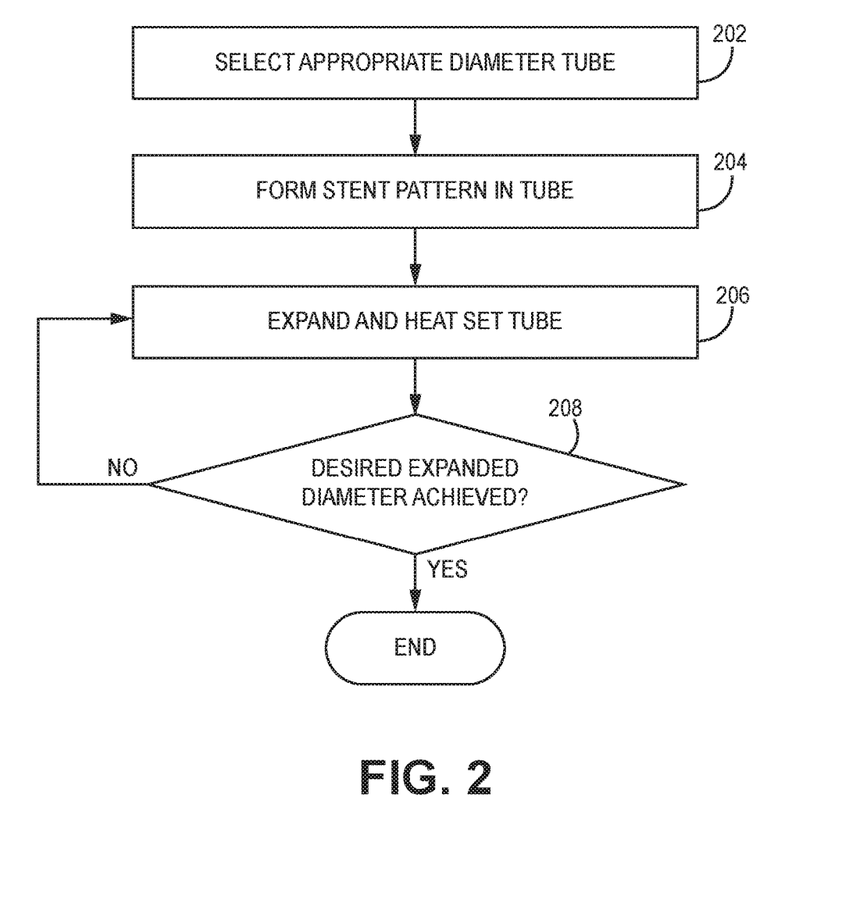
FIG. 2 is a flow chart diagram illustrating an example method of manufacture of the stent shown in FIGS. 1A-1C.

FIG. 2 is a flow diagram illustrating an example method of manufacture of the stents shown in FIGS. 1A-1C. In accordance this process of manufacture, a tube, such as a nitinol tube having an appropriate defined diameter is selected (202). For a venous application, the stent may require a greater wall thickness relative to arterial stents, e.g., approximately 0.45 mm for the 10, 12 and 14 mm stents and approximately 0.7 mm for the 16, 18 and 20 mm stents. The tube is then positioned with respect to a laser. The laser, which is programmed to provide the stent segment pattern of the stent body 100 described hereinabove, is activated to form the stent segment pattern (204).

In examples in which the stent is self-expandable and, therefore, formed from a self-expanding material, the cut tube is then subjected to a shape-setting process in which the cut tube is expanded on a mandrel and then heated (206). Multiple incremental expansions and heating cycles may be used to shape-set the stent body 100 to a desired expanded diameter (208). In some examples, the final expanded diameter may be equal to the desired deployed diameter of the stent body 100. The stent body 100 may be axially restrained such that the length of stent does not change during expansion.

Figure 3:
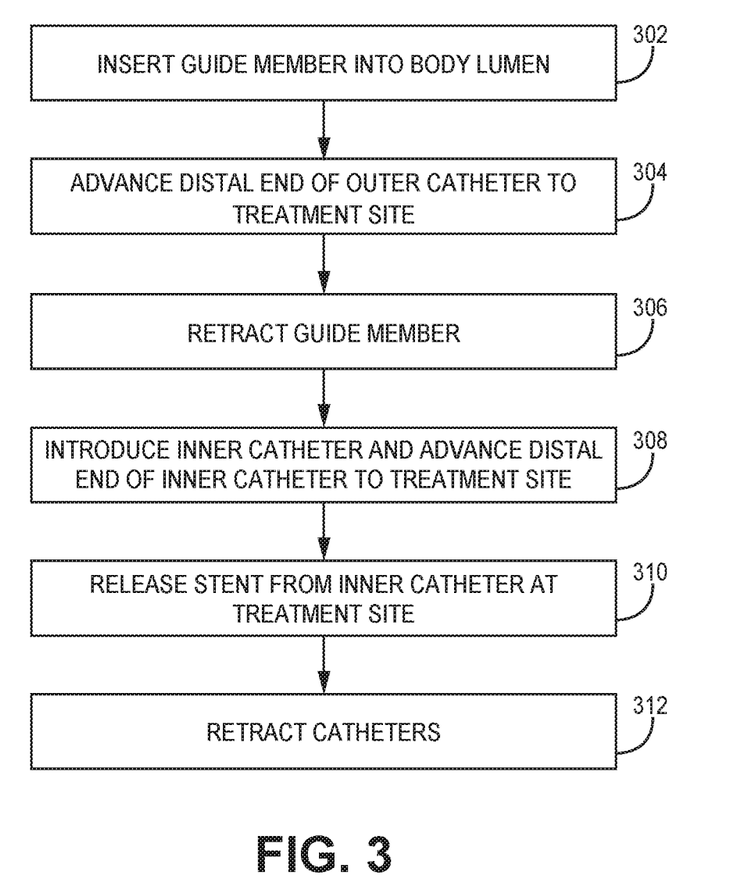
FIG. 3 is a flow chart illustrating an example method of implanting the stent shown in FIGS. 1A-1C.

FIG. 3 is a flow diagram illustrating an example method of implanting the stents shown in FIGS. 1A-1C. A guide member may be introduced into a body lumen of a patient (302). The guide member may be advanced though the body lumen to position a leading end (distal end) of the guide member at a target location as determined by a clinician. In some examples, the guide member may include a guidewire, a guide catheter, or both a guidewire and a guide catheter.

An outer catheter may be introduced over the guide member, or, in some examples, within the guide member, and a distal portion of the outer catheter may be advanced substantially adjacent to the treatment site as determined by the clinician (304). The outer catheter may define an outer catheter lumen.

The guide member may be retracted to remove the guide member from the outer catheter lumen (306), while leaving the outer catheter in place.

In some examples, an inner catheter may be introduced within the outer catheter and a distal portion of the inner catheter may be advanced proximate to the treatment site (308). In some examples, the distal portion of an inner catheter may be advanced to be substantially aligned with the distal portion of the outer catheter. In such examples, a distal portion of the inner catheter may be secured to a stent, including the stent body 100 of FIGS. 1A-1C.

In some examples, both the outer catheter and inner catheter may be advanced to the target location simultaneously, with the inner catheter being inside the outer catheter and the stent being positioned between the inner catheter and the outer catheter. For example, the delivery device described in U.S. patent application Ser. No. 14/256,136 naming inventors Senness et al., which is entitled, "STENT DELIVERY SYSTEM" and is incorporated herein by reference in its entirety, may be used to deliver any of the stents described herein. In such examples, the outer catheter may help retain the stent relative to the inner catheter.

The stent may be released from the inner catheter lumen and to the treatment site (310). For example, in some examples, a plunger may be advanced within the inner catheter lumen to push the stent from a distal portion of the inner catheter lumen. A clinician may control the plunger to advance the plunger such that the stent is advanced from the inner catheter.

In other examples, the stent may be positioned between the inner and outer catheters, and the outer catheter may be retracted with respect to the inner catheter and stent to allow for release of the stent from the inner catheter.

As the stent is released from a distal end of the inner catheter lumen or from around an outer surface of the inner catheter, the stent may expand such that it is secured against the wall of the body lumen and anchors the stent within the body lumen. In other examples, the stent may be expanded via a balloon or other mechanism.

After satisfactory delivery of the stent, other elements, including, for example, the outer catheter, an inner catheter, and/or a plunger may be removed from the body lumen (312).

Various examples have been described. These and other examples are within the scope of the following claims.

What is claimed is:

1. A stent comprising:
    a stent body defining a longitudinal axis and proximal and distal ends, the stent body being expandable from a compressed configuration to an expanded configuration, the stent body including a plurality of stent segments,
    wherein the stent segments include a first end segment and a second end segment on opposite ends of the stent body and at least one intermediate segment disposed between the first end segment and the second end segment,
    wherein each stent segment defines a plurality of cells,
    wherein each stent segment defines a plurality of peaks and valleys,
    wherein the at least one intermediate segment defines only x number of cells,
    wherein the first end segment defines at least x+1 number of cells, each of the cells of the first end segment being substantially equal in size,
    wherein the at least one intermediate segment defines only y number of peaks and valleys,
    wherein the first end segment defines only y number of peaks and valleys,
    wherein, for all of the intermediate segments between the first end segment and the second end segment, each cell of the x number of cells defined by the intermediate segments are larger than each of the cells of the first end segment, and
    wherein the first end segment includes a first circumferential row of struts and a second circumferential row of struts defining each of the cells of the first end segment, wherein the second circumferential row of struts is directly adjacent to the first circumferential row of struts, wherein the first circumferential row of struts includes a first peak and a first valley, the first peak pointing away from a longitudinal center of the first end segment and the first valley pointing towards the longitudinal center of the first end segment, wherein the second circumferential row of struts includes a second peak and a second valley, the second peak pointing towards the longitudinal center of the first end segment and the second valley pointing away from the longitudinal center of the first end segment, and wherein the first circumferential row of struts and the second circumferential row of struts are connected to each other between the first valley and the second peak.

2. The stent of claim 1, wherein a portion of the first end segment defining only one cell defines only three peaks, only two valleys, and only two half valleys, on each of two opposing sides of the portion of the first end segment.

3. The stent of claim 1, wherein a portion of the at least one intermediate segment defining only one cell defines only four peaks, only three valleys, and only two half valleys, on each of two opposing sides of the portion of the intermediate segment.

4. The stent of claim 1, wherein the second end segment defines at least x+1 number of cells.

5. The stent of claim 1, wherein each of the cells of the second end segment are substantially equal in size.

6. The stent of claim 5, wherein a portion of the second end segment defining only one cell defines only three peaks, only two valleys, and only two half valleys, on each of two opposing sides of the portion of the second end segment.

7. The stent of claim 1, wherein each of the cells of the at least one intermediate segment are substantially equal in size.

8. A method comprising:
    forming a stent pattern in a tubular member to form a stent body defining a longitudinal axis and proximal and distal ends, the stent body being expandable from a compressed configuration to an expanded configuration, the stent body including a plurality of stent segments,
    wherein the stent segments include a first end segment and a second end segment on opposite ends of the stent body and at least one intermediate segment disposed between the first end segment and the second end segment,
    wherein each stent segment defines a plurality of cells,
    wherein each stent segment defines a plurality of peaks and valleys,
    wherein the at least one intermediate segment defines only x number of cells,
    wherein the first end segment defines at least x+1 number of cells, each of the cells of the first end segment being substantially equal in size,
    wherein the at least one intermediate segment defines only y number of peaks and valleys,
    wherein the first end segment defines only y number of peaks and valleys,
    wherein, for all of the intermediate segments between the first end segment and the second end segment, each cell of the x number of cells defined by the intermediate segments are larger than each of the cells of the first end segment, and
    wherein the first end segment includes a first circumferential row of struts and a second circumferential row of struts defining each of the cells of the first end segment, wherein the second circumferential row of struts is directly adjacent to the first circumferential row of struts, wherein the first circumferential row of struts includes a first peak and a first valley, the first peak pointing away from a longitudinal center of the first end segment and the first valley pointing towards the longitudinal center of the first end segment, wherein the second circumferential row of struts includes a second peak and a second valley, the second peak pointing towards the longitudinal center of the first end segment and the second valley pointing away from the longitudinal center of the first end segment, and wherein the first circumferential row of struts and the second circumferential row of struts are connected to each other between the first valley and the second peak.

9. The method of claim 8, wherein the tubular member comprises shape-memory material.

10. The method of claim 8, further comprising incrementally expanding and heat setting the tubular member.

11. The method of claim 8, wherein a portion of the first end segment defining only one cell defines only three peaks, only two valleys, and only two half valleys, on each of two opposing sides of the portion of the first end segment.

12. The method of claim 8, wherein a portion of the at least one intermediate segment defining only one cell defines only four peaks, only three valleys, and only two half valleys, on each of two opposing sides of the portion of the intermediate segment.

13. The method of claim 8, wherein the second end segment defines at least x+1 number of cells.

14. The method of claim 8, wherein each of the cells of the second end segment are substantially equal in size.

15. The method of claim 8, wherein a portion of the second end segment defining only one cell defines only three peaks, only two valleys, and only two half valleys, on each of two opposing sides of the portion of the second end segment.

16. The method of claim 8, wherein each of the cells of the at least one intermediate segment are substantially equal in size.

17. The method of claim 8, wherein a portion of the first end segment defining only one cell defines only two peaks, only two half peaks, and only three valleys on each of two opposing sides of the portion of the first end segment.

18. A method comprising:
  advancing a distal end of a catheter to a treatment site within a patient, wherein a stent is disposed within the catheter;
  releasing the stent from the catheter at the treatment site, the stent comprising:
    a stent body defining a longitudinal axis and proximal and distal ends, the stent body being expandable from a compressed configuration to an expanded configuration, the stent body including a plurality of stent segments,
    wherein the stent segments include a first end segment and a second end segment on opposite ends of the stent body and at least one intermediate segment disposed between the first end segment and the second end segment,
    wherein each stent segment defines a plurality of cells,
    wherein each stent segment defines a plurality of peaks and valleys,
    wherein the at least one intermediate segment defines only x number of cells,
    wherein the first end segment defines at least x+1 number of cells, each of the cells of the first end segment being substantially equal in size,
    wherein the at least one intermediate segment defines only y number of peaks and valleys,
    wherein the first end segment defines only y number of peaks and valleys,
    wherein, for all of the intermediate segments between the first end segment and the second end segment, each cell of the x number of cells defined by the intermediate segments are larger than each of the cells of the first end segment, and
    wherein the first end segment includes a first circumferential row of struts and a second circumferential row of struts defining each of the cells of the first end segment, wherein the second circumferential row of struts is directly adjacent to the first circumferential row of struts, wherein the first circumferential row of struts includes a first peak and a first valley, the first peak pointing away from a longitudinal center of the first end segment and the first valley pointing towards the longitudinal center of the first end segment, wherein the second circumferential row of struts includes a second peak and a second valley, the second peak pointing towards the longitudinal center of the first end segment and the second valley pointing away from the longitudinal center of the first end segment, and wherein the first circumferential row of struts and the second circumferential row of struts are connected to each other between the first valley and the second peak.

19. The method of claim 18, further comprising:
  inserting a guide member into a body lumen of the patient; and
  advancing the distal end of the catheter to the treatment site over the guide member.

20. The stent of claim 1, wherein the first end segment defines at least x+1 number of cells, each of the cells of the first end segment being substantially equal in size when the stent body is in an expanded state.

* * * * *